US00PP31448P2

(12) United States Plant Patent
Bourne

(10) Patent No.: US PP31,448 P2
(45) Date of Patent: Feb. 18, 2020

(54) GRAPEVINE NAMED 'SV30-28-449'

(50) Latin Name: *Vitis vinifera*
Varietal Denomination: SV30-28-449

(71) Applicant: Sunview Vineyards of California, Inc., Delano, CA (US)

(72) Inventor: Timothy F. Bourne, Visalia, CA (US)

(73) Assignee: Sunview Vineyards of California, Delano, CA (US)

( * ) Notice: Subject to any disclaimer, the term of this patent is extended or adjusted under 35 U.S.C. 154(b) by 0 days.

(21) Appl. No.: 16/350,208

(22) Filed: Oct. 11, 2018

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
CPC ..... A01H 5/0812
See application file for complete search history.

*Primary Examiner* — Kent L Bell
(74) *Attorney, Agent, or Firm* — Baker Manock & Jensen, PC; Eric C. Cole

(57) ABSTRACT

A new and distinct variety of grapevine plant named 'SV30-28-449' particularly characterized by its ellipsoidal shaped, seedless black skinned berries which are large, sweet, slightly aromatic and have crisp texture. Productivity is moderate, with a mixture of spur and cane pruning required to achieve a full crop.

2 Drawing Sheets

Latin name of the genus and species of the plant claimed: The plant claimed relates to a new and distinct variety of *Vitis vinifera*.

Variety denomination: The plant claimed shall be known as 'SV30-28-449'.

STATEMENT OF ANY FEDERALLY-SPONSORED RESEARCH AND DEVELOPMENT

The present invention is not subject of Federally-sponsored research or development.

BACKGROUND OF THE INVENTION

The present invention comprises a new and distinct cultivar of grapevine botanically known as *Vitis vinifera* and hereinafter referred to as grapevine named 'SV30-28-449'. As used herein, 'grapevine' refers to all plant parts including, vines, canes, tendrils, leaves, fruit and roots of grapevine named 'SV30-28-449'. Grapevine named 'SV30-28-449' is the result of an effort to produce a mid-season black, seedless table grape with fruit characteristics superior to the currently available public cultivar 'Unknown black' (unpatented). This new cultivar originated from a cross conducted in May 2009 near McFarland, Calif. between seeded grapevine plant selection 'SV22-88e-506' (unpatented) and pollen parent 'Princess' (unpatented). Clusters of fruit resulting from the hybridization were harvested at maturity, the seeds collected and stratified for three months at 1° C. The seeds were then planted in a standard greenhouse flat and the seedlings grown in the greenhouse at 26.4° C. with 12 hours' illumination under high pressure sodium vapor lamps. The seedling population of 254 plants was planted in the field in the spring of 2010 near Delano, Calif. The new grapevine was selected from this seedling population on Aug. 27, 2012. It was then propagated by cuttings and bench grafted to 'Freedom' (unpatented) rootstock in 2013. The present invention has been found to retain its distinctive characteristics through two successive asexual propagations using woody cuttings.

Grapevine named 'SV30-28-449' differs from its female parent grapevine 'SV22-88e-506' (unpatented) in that grapevine named 'SV30-28-449' is seedless while female parent grapevine 'SV22-88e-506' (unpatented) has hard seeds.

Grapevine named 'SV30-28-449' differs from its male parent 'Princess' (unpatented) in that grapevine named 'SV30-28-449' has black skinned berries while male parent 'Princess' (unpatented) has green skinned berries.

Grapevine named 'SV30-28-449' differs from the commercial cultivar 'Sugrasixteen' (U.S. Plant Pat. No. 11,749) in that grapevine named 'SV30-28-449' has larger berries than 'Sugrasixteen' (U.S. Plant Pat. No. 11,749) and ripens in late August while 'Sugrasixteen' (U.S. Plant Pat. No. 11,749) ripens in mid-July. Grapevine named 'SV30-28-449' differs from commercial cultivar 'Unknown black' (unpatented) in that grapevine named 'SV30-28-449' has berries which are black with ellipsoidal shape while 'Unknown black' (unpatented) has reddish black berries which are cylindrical in shape.

SUMMARY OF THE INVENTION

The following are the most outstanding and distinguishing characteristics of the ripe fruit of this new variety when grown under normal horticultural practices near McFarland, Calif. Some of the characteristics may vary depending upon changes in crop load and change of location of cultivation.

1. Black berry color;
2. Very firm berry texture; and
3. Large, ellipsoidal shaped berries with sweet, aromatic taste.

BRIEF DESCRIPTION OF THE DRAWINGS

This new grapevine is illustrated by the accompanying photographs which show fruit clusters, leaves, canes, and tendrils. The colors shown are as true as can be reasonably obtained by conventional photographic procedures. The first photograph of shoots, leaves and a fruit cluster taken from a five year old plant grown in a field near McFarland, Calif. in 2018. The second photograph was taken in 2018 of a cluster of fruit on a three year old vine, grown in a field near Bakersfield, Calif.

DETAILED BOTANICAL DESCRIPTION

Figure 1:
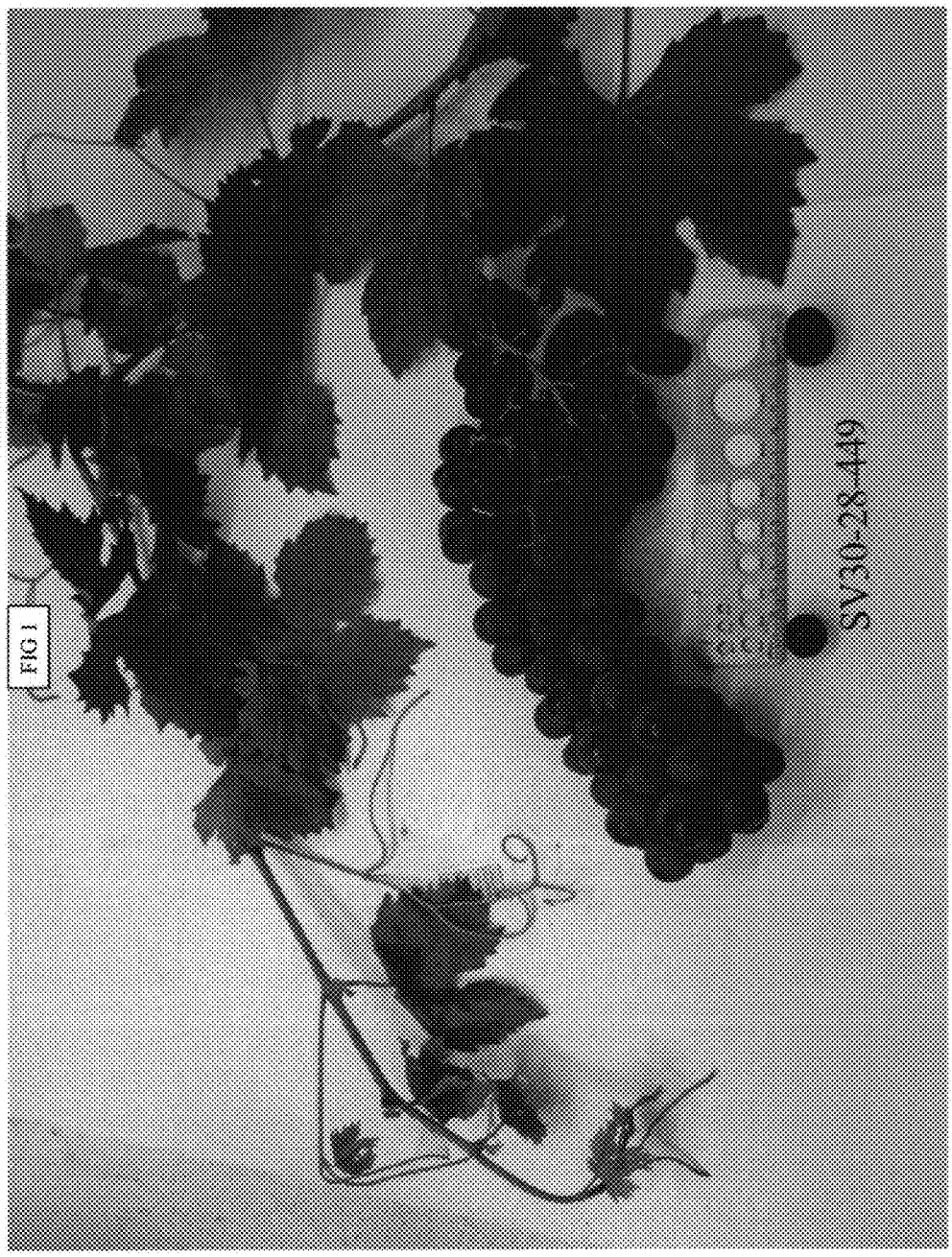
FIG. 1 Fruit cluster with shoots, leaves, tendrils and shoot tips from a vine sprayed with gibberellic acid.
Figure 2:
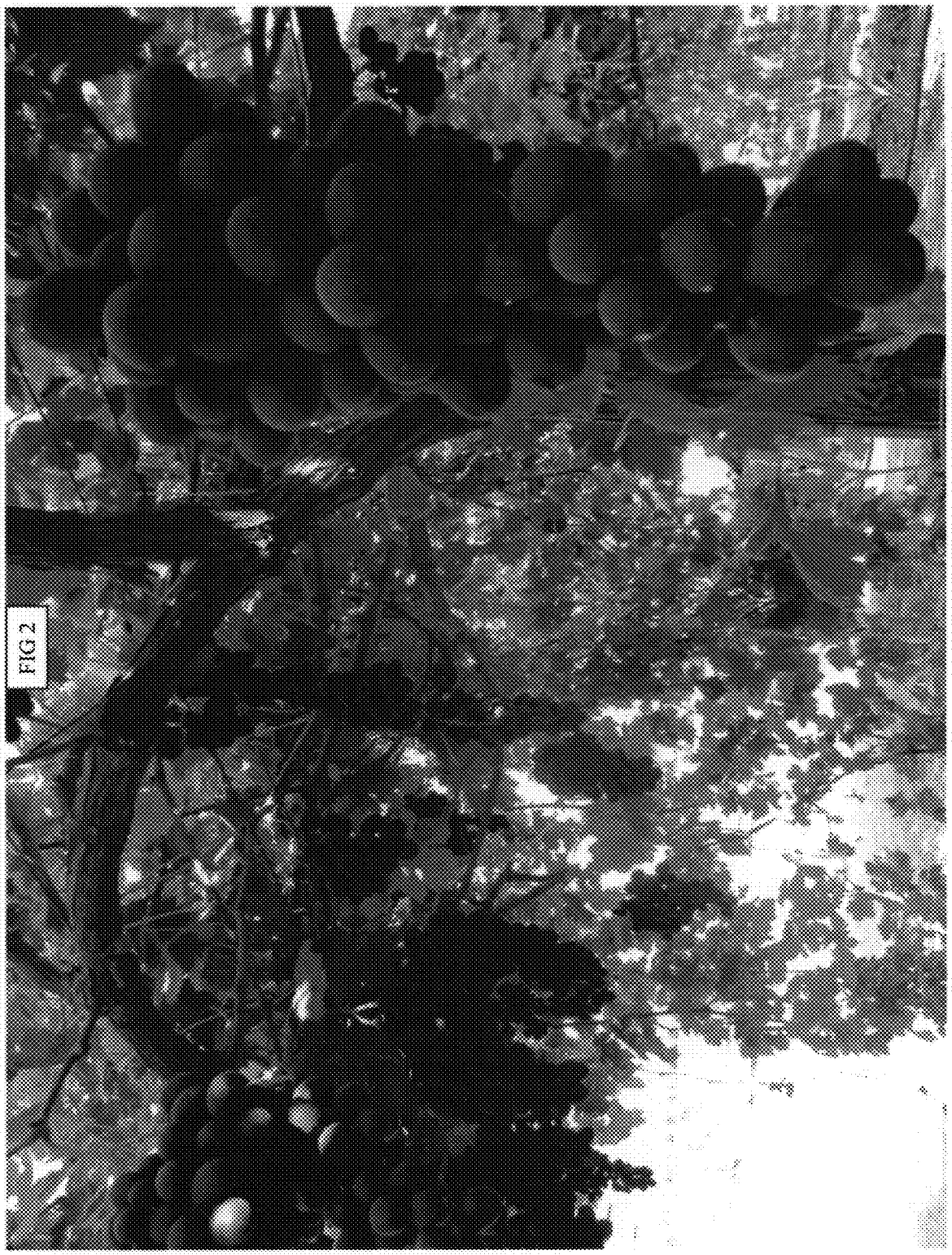
FIG. 2 Fruit clusters on vine sprayed with gibberellic acid.

The following detailed description sets forth the distinctive characteristics of grapevine named 'SV30-28-449'. Descriptions of the new invention apply to vines of grapevine named 'SV30-28-449' grown on 'Freedom' (unpatented) rootstock at a density of 1,537 vines per hectare grown near McFarland, Calif. in 2018. These vines were in their fourth year of full production, having been planted in 2013. These descriptions are believed to apply generally to the new variety grown under similar circumstances elsewhere. References to color correspond to The Royal Horticultural Society's Colour Chart, The Royal Horticultural Society, London, United Kingdom. Descriptors used herein conform to those set forth by the International Board for Plant Genetic Resources Institute Grape Descriptors (*Vitis* spp.) of 1983 and/or 1997 which were developed in collaboration with the Office International de la Vigne et du Vin (OIV) and the International Union for the Protection of New Varieties of Plants (UPOV) and published in *Descriptors for Grapevine* (*Vitis spp.*) (Anonymous, International Plant Genetic Resources Institute, 1997, ISBN 92-9043-352-3).

Classification:

*Family*.—Vitaceae.

*Botanical name*.—*Vitis vinifera*.

*Variety name*.—'SV30-28-449'.

Plant:

*Vigor*.—Averaging 247 cm of growth per cane; vines spur-pruned and shoot thinned to 32 shoots.

*Density of foliage*.—Moderate.

*Productivity*.—Very productive when pruned to spurs with canes, up to 32,000 kg/hectare.

*Hardiness*.—Hardiness observed to 0° C.

*Rootstock*.—'Freedom' (unpatented).

Trunk:

*Shape*.—Broadly elliptical.

*Straps*.—Long, split.

*Surface texture*.—Shaggy.

*Inner bark color*.—RHS Greyed orange group 174C.

*Outer bark color*.—RHS Brown group 177B.

Growing tips:

*Apex*.—Open.

*Density of prostrate hairs on tip*.—Sparse.

*Density of erect hairs on tip*.—Absent.

*Color*.—RHS Yellow Green Group 144B.

*Anthocyanins*.—Present at the tips of the young, expanding leaves: RHS Red purple group 64B.

*Shape*.—Flattened.

*Shoot attitude*.—Erect.

Young shoot:

*Density of erect hairs on node*.—Absent.

*Density of erect hairs on internode*.—Absent.

*Density of prostrate hairs on node*.—Sparse.

*Density of prostrate hairs on internode*.—Sparse.

*Internode color, lower surface*.—RHS Yellow green group 144B.

*Internode color, upper surface, in sun*.—RHS Red purple group 61A.

Young leaves:

*Color of young leaves*.—RHS Yellow Green group 144A.

*Density of prostrate hairs, lower surface, between veins*.—Absent.

*Density of erect hairs lower surface*.—Sparse, only at base of main veins.

*Density of prostrate hairs on main veins, lower surface*.—Sparse.

Mature leaves:

*Average blade length*.—14.2 cm.

*Average blade width*.—20.7 cm.

*Size of blade*.—Large.

*Shape*.—Pentagonal.

*Anthocyanin coloration of main veins on the upper side of the blade*.—Slight; restricted to the bases of main veins on sun exposed leaves: RHS Red purple group 65A to 63A.

*Mature leaf profile*.—Undulating, cupped upwards and flattened within plane of blade.

*Blistering* (*upper surface*).—Absent.

*Leaf blade tip*.—Apex points downward.

*Margins*.—Lobed, serrated, undulating.

*Apex*.—Broadly acuminate.

*Bases*.—Sagittate.

*Thickness*.—Medium.

*Undulation of blade between main and lateral veins*.—Slight.

*Shape of teeth*.—Conical; mixture of both sides straight and both sides convex.

*Length of teeth*.—2-11 mm.

*Ratio length/width of teeth*.—About 1.3: 1, slightly longer than wide.

*General shape of petiole sinus*.—Slightly open.

*Tooth at petiole sinus*.—Absent.

*Petiole sinus limited by veins*.—Absent.

*Shape of upper lateral sinus*.—Closed.

*Prostrate hairs between veins* (*lower surface*).—Absent.

*Erect hairs between veins* (*lower surface*).—Absent.

*Prostrate hairs on main veins* (*lower surface*).—Sparse.

*Density of erect hairs on main veins* (*lower surface*) .—Sparse, limited to junctions of main veins.

*Prostrate hairs on main veins* (*upper surface*).—Sparse, limited to bases of main veins.

*Upper surface*.—Summer color: RHS Green group 139A. Surface texture: Smooth. Surface appearance: Dull. Goffering of blade: Absent.

*Lower surface*.—Summer color: RHS Green group 141A. Anthocyanin coloration of main veins on lower leaf surface: Absent. Anthocyanin coloration on laterals: No. Glossiness: Low. Pubescence: Absent. Surface texture: Rough. Surface appearance: Dull.

*Petiole*.—Diameter (typical): 2.5 mm. Diameter (observed): 2.5 mm. Length: 12.6 cm. Length of petiole compared to middle vein: Slightly shorter. Density of prostrate hairs: Absent. Density of erect hairs: Absent. Shape of base of petiole sinus: Slightly open.

Color: In shade: RHS Yellow green group 144C. In sun: RHS Red purple group 61B.

Tendrils:

*Length (typical)*.—26.5 cm.

*Length (observed)*.—26.5 cm.

*Color*.—In shade: RHS Yellow green group 144C.

*Form*.—Bifurcated or trifurcated.

*Number of successive tendrils*.—At most, 2.

*Density of prostrate hairs*.—Absent.

Flowers:

*Flower sex*.—Perfect.

*Position of first flowering nodes*.—Usually on node 4.

*Number of inflorescences per shoot*.—One cluster on about 50% of shoots on vines pruned to spurs.

*Length of inflorescences*.—16.5 cm.

*Calyptra color*.—RHS yellow green group 143B.

*Ovary length*.—2.5 mm.

*Ovary width*.—1.0 mm.

*Ovary color*.—RHS Green group 141B.

*Filament color*.—Translucent, absent of pigmentation.

*Anther length*.—1 mm.

*Anther color*.—RHS Yellow group 4A.

*Date of full bloom*.—May 11th.

Fruit:

*Ripening period*.—Mid-season.

*Date of ripening*.—August 29th at McFarland, Calif.

*Use*.—Fresh market.

*Keeping quality*.—Good.

*Shipping quality*.—Good.

*Solids-sugar*.—21 brix at full maturity.

*Refractometer test*.—19.5 brix.

*Cluster*.—

*Bunch*.—Size: Medium. Natural cluster weight (typical): 455 g. Natural cluster weight (observed): 455 g. Length (peduncle excluded): 22.8 cm. Width: 9.3 cm. Weight: With gibberellic acid treatment: 535 g. Density: Well-filled. Number of berries: 90. Form: Conical to cylindrical.

*Peduncle*.—Diameter (typical): 4 mm. Diameter (observed): 4 mm. Length: 4.3 cm. Lignification: Slight, confined to about 6 mm at the base. Color: RHS Yellow green group 144A.

*Berry*.—Size: Medium large. Weight: Natural berry weight (typical): 5.0 g. Natural berry weight (observed): 5.0 g. With gibberellic acid treatment: about 5.4 g. Shape: Ellipsoidal. Presence of seeds: Seedless; most berries develop one or two tiny ovule traces about 5 mm in length. Cross section: Circular. Dimensions: Longitudinal axis: About 2.5 cm. Horizontal axis: About 2.0 cm. Skin color (without bloom): RHS Black group 202A except at cap stem: RHS Red purple group 60A. Flesh color: Translucent, absent of color. Juiciness of flesh: Very juicy. Berry firmness: Very firm. Particular flavor: Slightly aromatic, typical *Vitis vinifera* table grape. Bloom (cuticular wax): Heavy. Pedicel length: About 1.0 cm. Pedical diameter (typical): 1.5 cm. Pedical diameter (observed): 1.5 cm. Pedical color: RHS Yellow green group 144 C. Berry separation from pedicel: Difficult. Skin: Thickness: Medium. Texture: Berry crisp. Reticulation: Absent. Roughness: Absent. Tenacity: Tenacious to flesh. Tendency to crack: Resistant.

Disease and insect resistance: Moderately susceptible to powdery mildew which may be controlled with standard fungicides in California.

Having thus described and illustrated our new variety of grapevine, we claim:

1. A new and distinct variety of grapevine plant named 'SV30-28-449' substantially as illustrated and described herein.

* * * * *